United States Patent
Bernstein

(10) Patent No.: US 7,320,708 B1
(45) Date of Patent: Jan. 22, 2008

(54) CERVICAL INTERBODY DEVICE

(75) Inventor: Avi Bernstein, Wilmette, IL (US)

(73) Assignee: SDGI Holdings, Inc., Wilmington, DE (US)

( * ) Notice: Subject to any disclaimer, the term of this patent is extended or adjusted under 35 U.S.C. 154(b) by 293 days.

(21) Appl. No.: 10/293,843

(22) Filed: Nov. 13, 2002

(51) Int. Cl.
A61F 2/44 (2006.01)
A61F 2/30 (2006.01)

(52) U.S. Cl. .................................. 623/17.15
(58) Field of Classification Search ............. 623/17.11, 623/17.12, 17.13, 17.14, 17.15, 17.16; 606/61
See application file for complete search history.

(56) References Cited

U.S. PATENT DOCUMENTS

| | | | |
|---|---|---|---|
| 5,062,850 A * | 11/1991 | MacMillan et al. ...... | 623/17.11 |
| 5,236,460 A * | 8/1993 | Barber .................... | 623/17.15 |
| 5,290,312 A | 3/1994 | Kojimoto et al. | |
| 5,336,223 A | 8/1994 | Rogers | |
| 5,360,430 A | 11/1994 | Lin | |
| 5,405,391 A | 4/1995 | Hednerson et al. | |
| 5,443,515 A | 8/1995 | Cohen et al. | |
| 5,458,641 A * | 10/1995 | Ramirez Jimenez ..... | 623/17.11 |
| 5,458,642 A * | 10/1995 | Beer et al. .............. | 623/17.13 |
| 5,534,029 A * | 7/1996 | Shima .................... | 623/17.15 |
| 5,723,013 A | 3/1998 | Jeanson et al. | |
| 5,776,197 A | 7/1998 | Rabbe et al. | |
| 5,827,328 A * | 10/1998 | Buttermann ............. | 623/17.13 |
| 5,865,848 A | 2/1999 | Baker | |
| 5,888,223 A | 3/1999 | Bray, Jr. | |
| 6,019,793 A * | 2/2000 | Perren et al. ............ | 623/17.16 |
| 6,063,121 A * | 5/2000 | Xavier et al. ............ | 623/17.15 |
| 6,066,175 A | 5/2000 | Henderson et al. | |
| 6,106,557 A | 8/2000 | Robioneck et al. | |
| 6,113,638 A | 9/2000 | Williams et al. | |
| 6,146,421 A * | 11/2000 | Gordon et al. ........... | 623/17.15 |
| 6,159,244 A | 12/2000 | Yoon | |
| 6,174,334 B1 | 1/2001 | Suddaby | |
| 6,176,881 B1 | 1/2001 | Schar et al. | |
| 6,190,413 B1 | 2/2001 | Sutcliffe | |
| 6,193,755 B1 | 2/2001 | Metz-Stavenhagen et al. | |
| 6,200,348 B1 | 3/2001 | Biedermann et al. | |
| 6,235,059 B1 | 5/2001 | Benezech et al. | |
| 6,296,647 B1 | 10/2001 | Robioneck et al. | |
| 6,296,665 B1 * | 10/2001 | Strnad et al. ............ | 623/17.16 |
| 6,299,644 B1 * | 10/2001 | Vanderschot ............ | 623/17.15 |
| 6,342,055 B1 | 1/2002 | Eisermann et al. | |
| 6,344,057 B1 | 2/2002 | Rabbe et al. | |
| 6,375,681 B1 | 4/2002 | Truscott | |
| 6,375,683 B1 | 4/2002 | Crozet et al. | |
| 6,395,030 B1 | 5/2002 | Songer et al. | |
| 6,395,034 B1 | 5/2002 | Suddaby | |
| 6,419,705 B1 | 7/2002 | Erickson | |
| 6,432,106 B1 | 8/2002 | Fraser | |
| 6,443,990 B1 * | 9/2002 | Aebi et al. ............... | 623/17.16 |
| 6,527,804 B1 * | 3/2003 | Gauchet et al. ......... | 623/17.12 |

(Continued)

*Primary Examiner*—Pedro Philogene
(74) *Attorney, Agent, or Firm*—Coats & Bennett, P.L.L.C.

(57) ABSTRACT

An interbody spacer assembly includes a pair of end pieces spaced apart by a connector extending between them. The end pieces extend generally parallel to the end plates of adjoining vertebral bodies. Fasteners connect the end pieces to the vertebral bodies. Bone graft material or solid bone can be placed in the interior space defined by the end pieces and connector, which bone graft material or solid bone eventually fuses together and to the adjoining end plates through the end pieces.

22 Claims, 3 Drawing Sheets

U.S. PATENT DOCUMENTS

| | | |
|---|---|---|
| 6,558,424 B2 * | 5/2003 | Thalgott .................. 623/17.16 |
| 6,562,074 B2 | 5/2003 | Gerbec et al. |
| 6,579,290 B1 | 6/2003 | Hardcastle et al. |
| 6,579,320 B1 * | 6/2003 | Gauchet et al. .......... 623/17.15 |
| 6,610,090 B1 | 8/2003 | Bohm et al. |
| 6,648,917 B2 | 11/2003 | Gerbec et al. |
| 6,682,561 B2 | 1/2004 | Songer et al. |
| 6,682,563 B2 | 1/2004 | Scharf |
| 6,712,852 B1 | 3/2004 | Chung et al. |
| 6,730,127 B2 | 5/2004 | Michelson |
| 6,830,589 B2 | 12/2004 | Erickson |
| 6,837,905 B1 | 1/2005 | Lieberman |
| 6,852,113 B2 | 2/2005 | Nathanson et al. |
| 6,852,129 B2 | 2/2005 | Gerbec et al. |
| 6,866,682 B1 | 3/2005 | An et al. |
| 2003/0163199 A1 | 8/2003 | Boehrn et al. |
| 2004/0044411 A1 | 3/2004 | Suddaby |
| 2004/0092929 A1 | 5/2004 | Zindrick |
| 2004/0162618 A1 | 8/2004 | Mujwid et al. |
| 2004/0199254 A1 | 10/2004 | Louis et al. |
| 2005/0113921 A1 | 5/2005 | An et al. |
| 2005/0234550 A1 | 10/2005 | Metz-Stavenhagen |

* cited by examiner

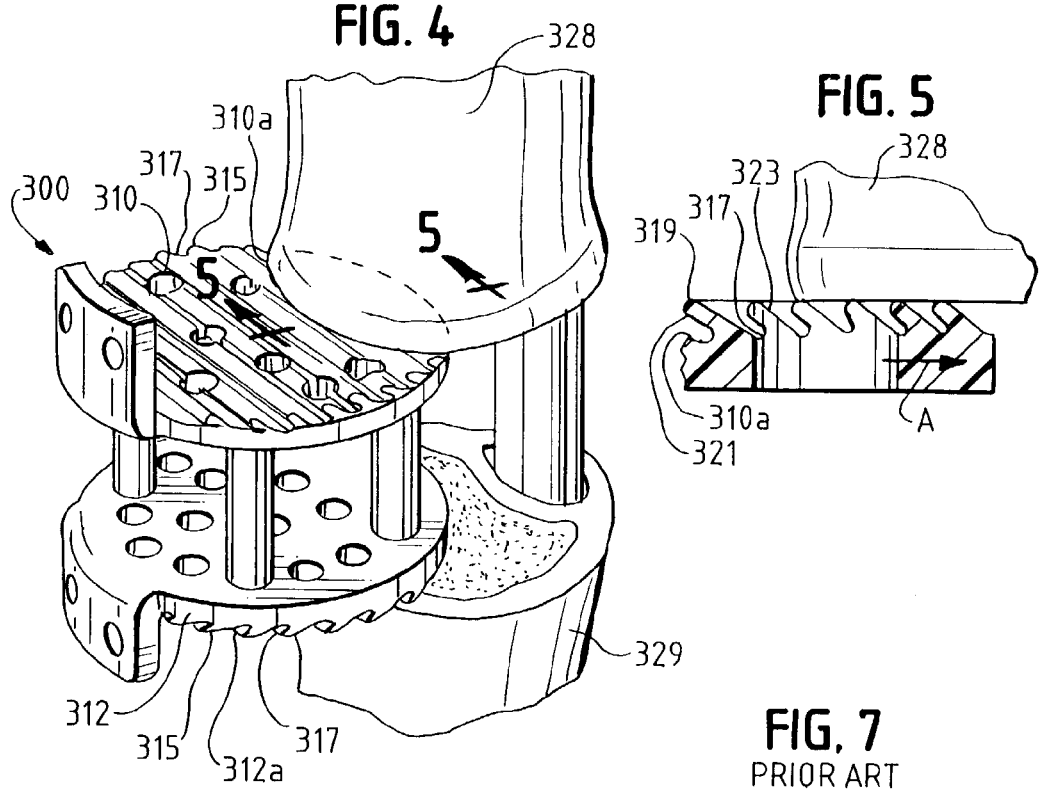
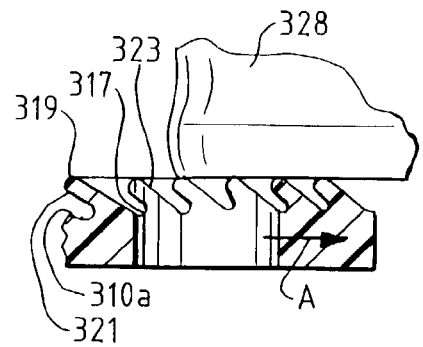
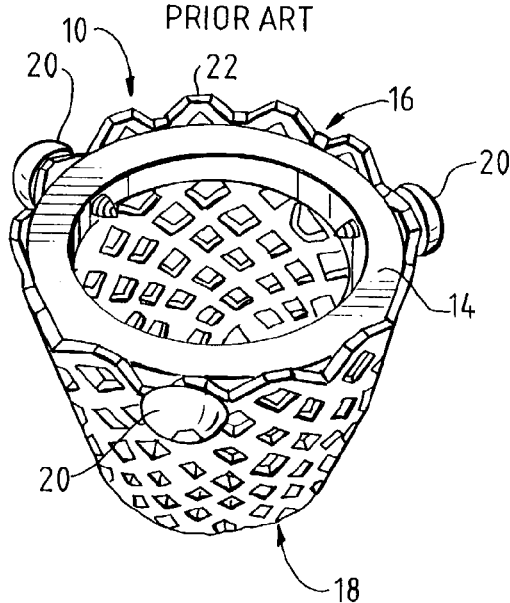
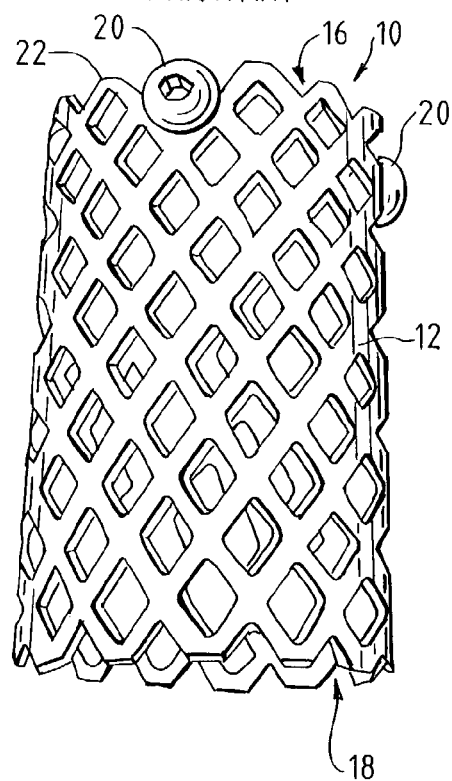

CERVICAL INTERBODY DEVICE

This invention relates to cervical spine supports, and, in particular, to a device that acts as a spacer between cervical vertebral bodies so that bone graft material inserted within the device can fuse and replace pathological bone removed surgically.

BACKGROUND OF THE INVENTION

It is known in the prior art to use cage-like spacers made of titanium mesh in tube shapes between vertebrae to provide support to the cervical spine. Spacers are needed when either the vertebrae or disk are removed for pathological reasons due to injury or disease. One such spacer 10 is shown in FIGS. 6 and 7. Such prior art spacers are typically formed from a mesh 12 rolled into a tube extending longitudinally for the length of the removed vertebra or disk. Rings 14 on both ends 16, 18 are intended to reinforce the mesh and maintain the desired diameter of the spacer and also connect to adjacent vertebrae with screws 20. Spacer 10 is filled with granular bone tissue which eventually fuse or graft together and with the healthy tissue above and below the spacer. The spacer maintains the granular bone tissue in place until the graft is complete. The prior art spacers are difficult to install between existing vertebrae and difficult to satisfactorily fill with such bone tissue. The corrugated ends 22 of the mesh often catch adjoining tissue as the spacer is being implanted between the desired vertebrae. The reinforcing rings 14 tend to collapse into the adjacent vertebrae and damage them, i.e., subsidence. The granular bone tissue placed within the mesh tends to fall out of the mesh during the positioning process, and the mesh makes it difficult to refill the spacer with additional bone tissue. Gaps between the bone tissue inside the cage often result, which cannot be readily detected or remedied. Consequently, the grafting process is slowed or results in a weakened graft or incomplete fusion and malalignment due to these gaps.

Consequently, a need exists for, and it is an object of this invention to provide, an improved cervical interbody device that is easier to install between cervical vertebral bodies and results in a stronger and more reliable graft.

SUMMARY OF THE INVENTION

According to the present invention, a spacer assembly is provided for use in spinal surgeries. The spacer assembly comprises two end pieces for interfacing with the end plates of adjacent vertebrae. Each end piece is generally disk-like in form and includes an inner surface facing the interior of the spacer and an outer surface facing the adjacent vertebrae. Each end piece has attached thereto a flange that extends longitudinally and exteriorly of the end piece. The end pieces are spaced and reinforced by one or more connectors. The spacer assembly engages the adjacent vertebral disks by engaging each flange with the adjacent vertebrae to couple the assembly and vertebrae together. The spacer assembly defines an interior region that is filled with morselized bone graft, structural bone graft, biologic fusion materials, or solid bone to fuse together and with the adjacent vertebrae, thereby replacing pathological bone or disk material removed surgically.

In a preferred embodiment, the end pieces are contoured to conform to the spinal cord. The end pieces are further designed to promote bone growth into the adjacent areas by, for instance, including apertures or an opening between the interior region and the vertebrae.

The inventive spacer assembly can be used to replace either a surgically removed disk (diskectomy) or vertebra (corpectomy).

BRIEF DESCRIPTION OF THE DRAWINGS

FIG. 4 is a perspective view of a third embodiment of the invention not yet implanted in the spine.

FIG. 5 is a partial side elevation view of an end piece of the embodiment of FIG. 4 which is not yet positioned in the spine as viewed along line 5 of FIG. 4.

FIG. 6 is a top perspective view of a prior art spacer.

FIG. 7 is a side perspective view of a prior art spacer.

DETAILED DESCRIPTION OF THE INVENTION

Figure 1:
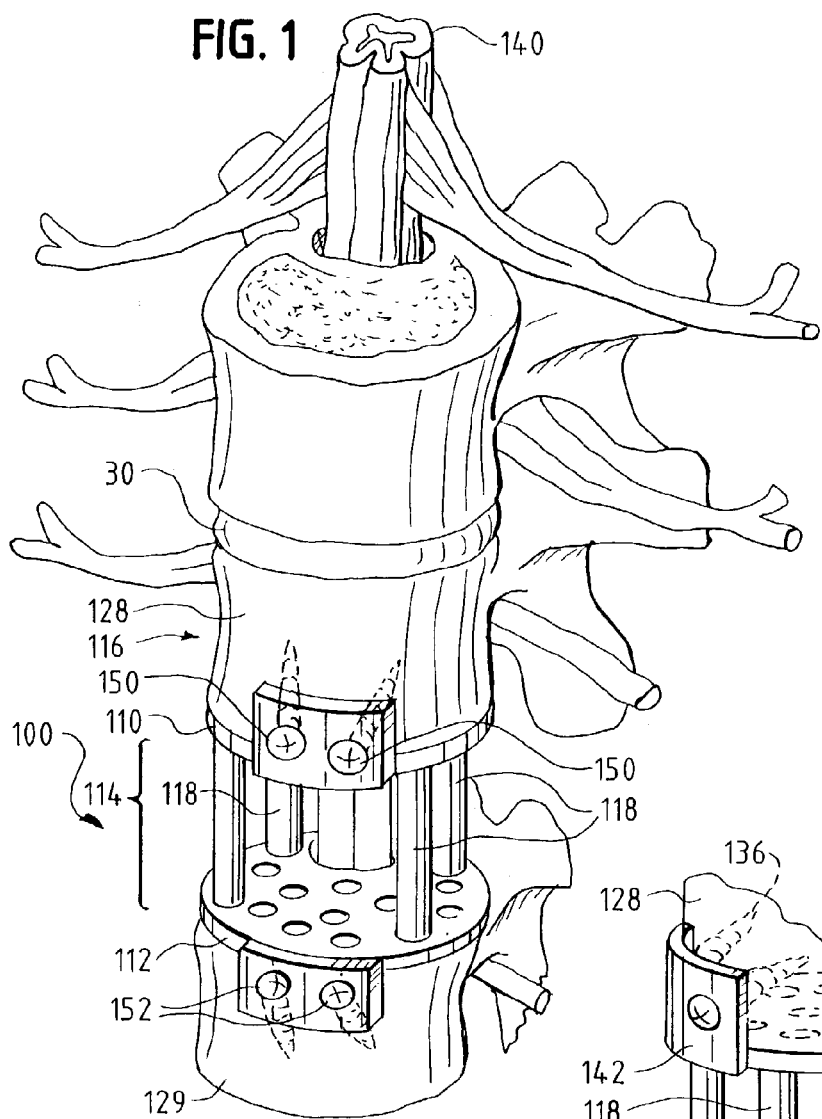
FIG. 1 is a front perspective view of the invention implanted in the spine.
Figure 2:
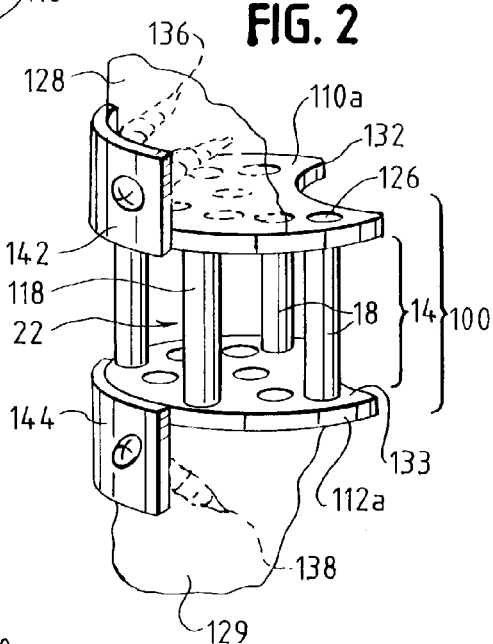
FIG. 2 is a side perspective view of the invention with the surrounding spine tissue partially cut-away.

As seen in FIGS. 1, 2, the inventive spacer assembly 100 includes an upper end piece 110 and a lower end piece 112 with connector 118 therebetween. The assembly 100 is located between the vertebral bodies of a spine 116 during surgery to maintain the vertebrae in a spaced-apart configuration. End pieces 110, 112 of the present invention are substantially parallel to the adjoining surfaces (often referred to as "end plates") of the vertebral bodies 128, 129 and are shaped and dimensioned to closely match the cross-sectional shape and dimensions of the end plates.

Connectors 118 comprise one or more rigid or semi-rigid posts for maintaining a desired distance between the end pieces 110, 112. For example, titanium posts 118, as seen in FIGS. 1 and 2, maintain the spacing between the end pieces so that granular bone material can be inserted between the end pieces in the interior region 114 defined by the assembly 100. The connectors 118 may be of equal length or they may be of different lengths. For example, if the anterior connectors (i.e. those farthest from the spinal cord 140) are longer than the posterior connectors (i.e. those closest to the spinal cord 140), lordosis can be maintained or restored. When the connectors are not of equal lengths, the end pieces are not parallel to each other, and that non-parallel relationship would be preferred in most cases to accommodate the natural curvature of the spine.

The end pieces 110, 112 are approximately disk-shaped to conform to the cross-sectional shape of the end plates of the adjacent vertebrae. The exterior surfaces 110a and 112a, respectively, of end pieces 110 and 112 interface with the end plates of adjacent vertebrae 128, 129. The end pieces are preferably contoured at 132, 134 to avoid compressing or otherwise affecting the spinal cord 140.

The interior region 114 between end pieces 110, 112 is substantially open around its circumference, and it can be easily filled with bone graft tissue to fuse to vertebral bodies 128, 129 of spine 116. The end pieces 110, 112 contain apertures 126 extending through their thickness to allow the bone graft tissue to grow through the end pieces and into the adjacent vertebrae, and thereby providing direct contact between the bone graft tissue and the adjoining vertebrae.

The end pieces 110, 112 have attached flanges 142, 144 projecting perpendicularly and exteriorly away from the end pieces 110, 112, respectively, and the flanges 142, 144 are located circumferentially around an anterior portion of the end pieces 110, 112, respectively. The flanges act as stops to engage the assembly in proper position relative to the spine. They also prevent retropulsion or compression of the spinal cord, which can occur if the assembly were to slide too far into the spine toward the spinal cord 140 or otherwise shift out of place. The flanges have holes 150, 152 for receiving screws 136, 138 of the type customarily used in spine surgeries. These screws 136, 138 are screwed into the adjacent vertebral bodies 128, 129 respectively, preferably with commonly available locking mechanisms, to secure the spacer assembly in place relative to the spine. Alternatively, screws could be located through apertures in the end pieces and directly into the vertebrae. Preferably, the screws are inserted through the flange at an angle toward or away from the adjoining end piece, rather than parallel thereto, to increase the stability of the device and reduce the possibility of inadvertent displacement.

Figure 3:
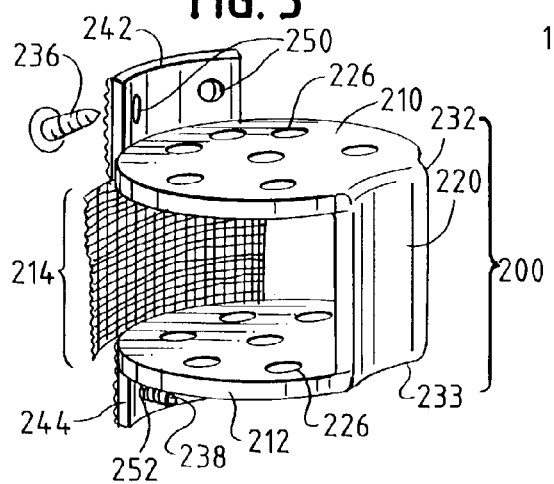
FIG. 3 is a perspective view of second embodiment of the invention.

A second embodiment of the invention is shown in FIG. 3. The spacer assembly 200 includes a pair of end pieces 210, 212 spaced apart by a connector 220. The connector 220 is in the form of a contoured wall that connects the end pieces at their peripheries where the end pieces are likewise contoured, i.e. at 232, 233. This embodiment also includes a mesh 221 that partially but does not entirely surround interior region 214 between the end pieces where the bone graft tissue is located and spans the distance between the end pieces. This mesh 221 is preferably located at the anterior side of assembly 200 and helps retain the bone graft tissue and prevent it from dislodging during implantation of the assembly 210. The mesh is held in place relative to the rest of assembly 210 by screws 236, 238 extending through the mesh, through holes 250, 252 of flanges 242, 244, and finally into the adjacent vertebrae. Thus, the mesh can be installed after the bone graft tissue is positioned. Like the first embodiment, end pieces 210, 212 each include multiple apertures 226 to permit the bone graft tissue in region 214 to fuse with the adjacent vertebrae. The remaining region 214 is not surrounded by mesh because a patient's muscle tissue along the spine will partially enclose the area 214. Preferably, mesh 221 has an arcuate width that is slightly larger than the arcuate width of flanges 242, 244. The connector 220 is located at the posterior side of the assembly, closest to the spinal cord, where it protects the spinal cord from the bone graft tissue. This embodiment can be supplemented with anteriorly-located connectors in the form of posts, such as those shown in FIGS. 1, 2, 4, if desired for additional strength.

A third embodiment of the invention appears in FIGS. 4, 5. This embodiment is a spacer assembly 300 that is essentially the same as the first embodiment, except that the exterior surfaces 310a and 312a of end pieces 310 and 312, respectively, are roughened or formed with alternating ridges 315 and valleys 317. The ridges are angled relative to the planes of surfaces 310a and 312a so that the peak 319 of each ridge 315 is on the anterior side (i.e. farthest from the spinal cord) of the ridge. Stated differently, the ridges are slanted so that the anterior side of each ridge (e.g. side 321) forms an angle less than 90 degrees with the plane of the exterior surface of the end piece (e.g. 310a), while the posterior side of each ridge (e.g. side 323) forms an angle greater than 90 degrees with the plane (e.g. 310a) of the exterior surface of the end piece. This arrangement permits the assembly 300 to easily slide laterally in the direction of arrow A between the spaced vertebrae 328, 329, while also resisting lateral movement in the opposite direction away from the spaced vertebrae. This helps prevent inadvertent dislocation of the assembly away from the desired position between the vertebrae.

Figure 8:
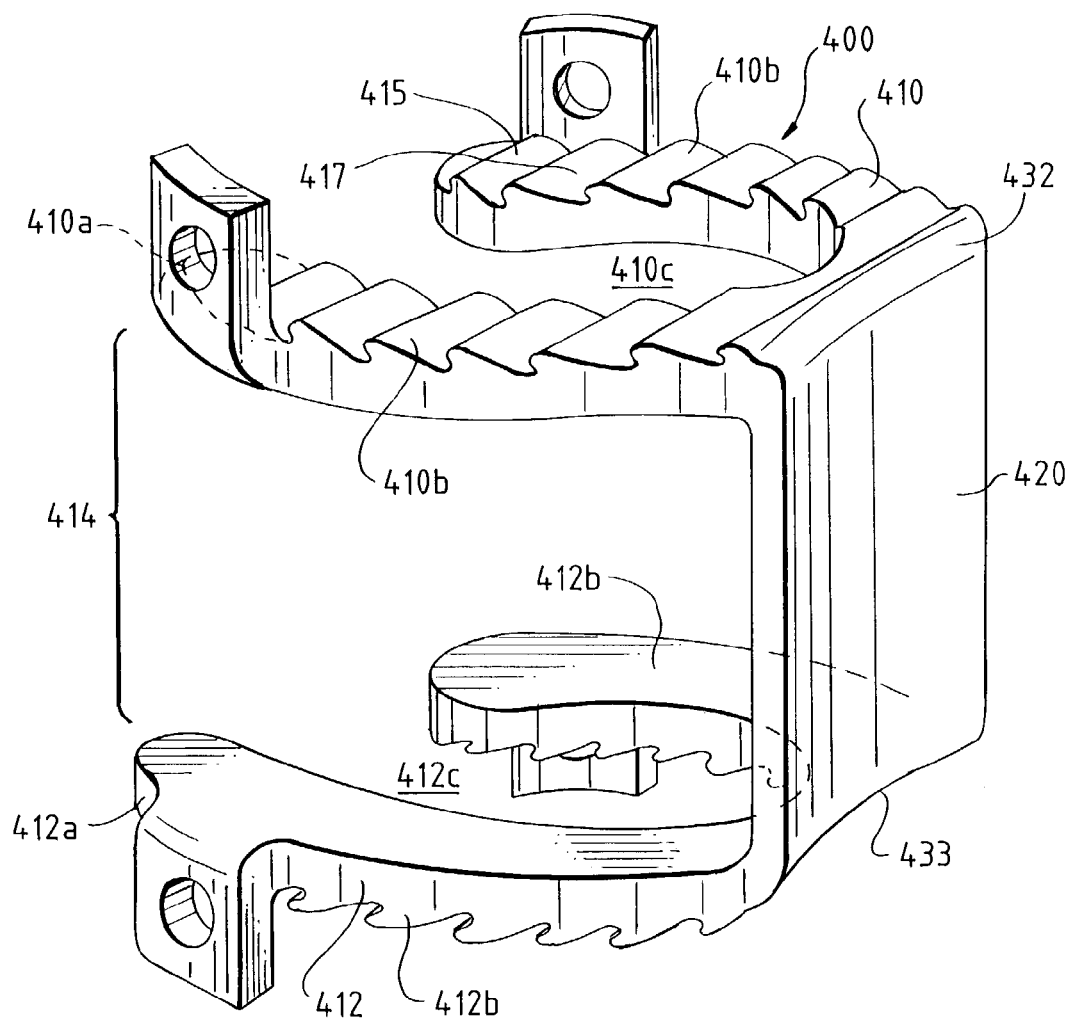
FIG. 8 is a perspective view of a fourth embodiment of the invention.

A fourth embodiment of the invention is shown in FIG. 8. In this embodiment, the spacer assembly 400 includes a pair of U-shaped end pieces 410, 412 which are spaced apart by a connector 420. The connector is the form of a contoured wall that connects the end pieces at their peripheries where the end pieces are closed and likewise contoured, i.e. at 432, 433. The end pieces include alternating ridges 415 and valleys 417, which are angled relative to the planes of exterior surfaces 410a and 412a of end pieces 410 and 412, respectively, similar to the ridges, valleys and planes of the third embodiment (FIG. 5). The U-shaped end pieces each have a pair of arms 410b, 412b which define openings 410c, 412c between the arms. These openings communicate with open interior region 414, which is between end pieces 410, 412 and partially bounded by connector 420. This embodiment is therefore adapted to receive solid, whole pieces of bone (not shown) rather than bone graft pieces. The solid bone can be inserted into region 414 and between arms 410b, 412b so as to abut the vertically adjacent vertebrae (not shown) above and below end pieces 410, 412. The spaces 410c, 412c permit the solid bone to fuse and heal with the adjoining vertebrae.

The end pieces and flanges are desirably composed of titanium or a bioabsorbable material, but they may also be composed of other rigid materials such as other metals and plastics. There is no need for adjuvant fixation, such as with a plate or another device to stabilize the position of the assembly.

The end pieces, flanges and connectors can be formed integrally, or they can be modular. A modular construction more easily permits the use of different size end pieces in the same assembly, as well as different length connectors.

The present invention has been described in connection with cervical vertebral bodies, but the same invention could be applied to the thoracic and lumbar spine by simply varying the shapes and dimensions of the components to correspond to the shapes and dimensions of the thoracic and lumbar vertebrae.

It should be recognized that, while the invention has been described in relation to a preferred embodiment, those skilled in the art may develop a wide variation of structural details without departing from the principles of the invention. Accordingly, the appended claims are to be construed to cover all equivalents falling within the scope and spirit of the invention.

The invention claimed is:

1. An interbody spacer assembly for replacing either a vertebra or disk, comprising:
    first and second end pieces, said end pieces spaced a fixed distance apart from each other;
    a non-adjustable connector extending between and connecting said first and second end pieces, said connector leaving an interior region between said end pieces for receiving bone graft material, said interior region being substantially open around its circumference;
    at least one fastener for securing the spacer assembly to a vertebral body; and
    a flange extending from a peripheral edge of at least one of said end pieces and configured to receive the at least one fastener.

2. The spacer assembly of claim 1 further comprising a retainer spanning said first and second end pieces for retaining bone graft material.

3. The spacer assembly of claim 1 wherein each of the end pieces is substantially disk-shaped.

4. The spacer assembly of claim 1 wherein the connector is a rod.

5. The spacer assembly of claim 1 wherein the connector is a wall.

6. The spacer assembly of claim 5 wherein the connector is positioned so that it can extend along the spinal cord.

7. The spacer assembly of claim 6 wherein the connector is curved.

8. An interbody spacer assembly for replacing either a vertebra or a disk, comprising:
   first and second end pieces, said end pieces spaced apart from each other;
   a fixed length connector extending between and connected to said first and second end pieces;
   at least one fastener for securing the spacer assembly to a vertebral body; and
   a flange extending from at least one of said end pieces, said flange cooperating with said at least one fastener for securing the spacer assembly to a vertebral body;
   wherein said end pieces have outer edges, and wherein said connector is a side wall extending from the outer edge of said first end piece to the outer edge of said second end piece.

9. The spacer assembly of claim 8 wherein said end pieces each include a plurality of apertures.

10. The spacer assembly of claim 8 wherein said end pieces each have a roughened exterior surface.

11. The spacer assembly of claim 10 wherein said roughened surfaces are comprised of alternating ridges and valleys.

12. The spacer assembly of claim 8 wherein said end pieces each comprise a pair of arms defining a space between said arms, and wherein said spaces between said arms communicate with the open interior region extending between said end pieces.

13. An interbody spacer assembly for replacing either a vertebra or disk, comprising:
   a pair of substantially disk-shaped end pieces, each of said end pieces approximating the cross-sectional dimensions of a vertebral body and having a plurality of apertures extending through said end pieces;
   a connector rigidly connecting and spacing said end pieces, said end pieces and connector defining an interior space;
   a flange extending from each of said pieces and away from said interior space;
   at least one fastener engaging the flange for securing said spacer assembly to a vertebral body; and
   a retainer extending between the end pieces for retaining bone graft material within said interior space.

14. An interbody spacer assembly comprising:
   a pair of end pieces each approximating the cross-sectional dimensions of a vertebral body;
   a connector extending between peripheral edges of the first and second end pieces, the connector rigidly connecting and spacing the end pieces; and
   an interior region formed by the first and second end pieces and the connector, the interior region having a fixed non-adjustable size and being substantially open to receive bone graft material.

15. The spacer assembly of claim 14 wherein the first and second end pieces are substantially flat.

16. The spacer assembly of claim 14 wherein the connector has a contoured shape to match the peripheral edges of the pair of end pieces.

17. The spacer assembly of claim 14 wherein the pair of end plates each comprise a pair of arms defining a space between said arm, and wherein said spaces between said arms communicate with the interior region.

18. The spacer assembly of claim 14 wherein the connector is positioned on a posterior side of the pair of end plates.

19. The spacer assembly of claim 14 further comprising at least one post within the interior region and extending between the pair of end pieces.

20. An interbody spacer assembly comprising:
   first and second end pieces that are spaced apart from each other;
   a connector connected to each of the first and second end pieces, the connector extending between and spacing apart the first and second end pieces;
   an interior region formed between the first and second end pieces and the connector, the interior region being substantially open and having a fixed non-adjustable size to receive bone graft material; and
   a flange extending from a peripheral edge of at least one of the first and second end pieces, and configured to receive a fastener to fasten the interbody spacer to a verterbral body.

21. The spacer assembly of claim 20 wherein the connector is attached along peripheral edges of the first and second end pieces.

22. The spacer assembly of claim 20, further comprising a plurality of connectors extending between the first and second end pieces.

* * * * *